Figure 2B:
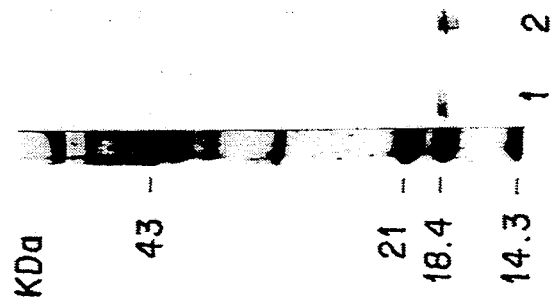

United States Patent [19]

Fuks et al.

[11] Patent Number: 5,362,641

[45] Date of Patent: Nov. 8, 1994

[54] HEPARANASE DERIVED FROM HUMAN SK-HEP-1 CELL LINE

[75] Inventors: Zvi Fuks, New York, N.Y.; Israel Vlodavsky, Gilo, Israel

[73] Assignee: Hadassah Medical Organization Kiryat Hadassah, Jerusalem, Israel

[21] Appl. No.: 768,900

[22] PCT Filed: Aug. 22, 1990

[86] PCT No.: PCT/US90/04772

§ 371 Date: Jan. 8, 1992

§ 102(e) Date: Jan. 8, 1992

[87] PCT Pub. No.: WO91/02977

PCT Pub. Date: Mar. 7, 1991

Related U.S. Application Data

[63] Continuation-in-part of Ser. No. 397,554, Aug. 23, 1989, abandoned.

[51] Int. Cl.$^5$ .................... C12N 9/26; C12N 9/24; C12N 9/42; C12N 9/14
[52] U.S. Cl. .................... 435/209; 435/200; 435/195; 435/201
[58] Field of Search ............... 424/94.1; 435/195, 201, 435/209

[56] References Cited

U.S. PATENT DOCUMENTS

| | | | |
|---|---|---|---|
| 4,401,758 | 8/1983 | Lormeau et al. | 435/84 |
| 4,481,195 | 11/1984 | Rubin | 435/180 |
| 4,560,661 | 12/1985 | Katsumata et al. | 435/183 |
| 4,584,368 | 4/1986 | Rubin | 536/4.1 |
| 4,716,038 | 12/1987 | Stanford et al. | 424/92 |
| 4,761,374 | 8/1988 | Beppu et al. | 435/232 |
| 4,859,581 | 8/1989 | Nicolson et al. | 435/13 |
| 4,882,318 | 11/1989 | Vlodavsky et al. | 514/56 |
| 5,279,824 | 1/1989 | Sawyer et al. | 435/201 |

OTHER PUBLICATIONS

Matzner et al. (1985). J. Clin. Invest (76), pp. 1306–1313.
Nakajima et al. (1984) Journal of Biological Chemistry (259), pp. 2283–2290.
Orenstein et al. (1978) Journal of Immunology (121), pp. 586–592.
Castellot Jr et al (1982) Journal of Biological Chemistry (257), pp. 11256–11260.
Naparstek et al (1984) Nature (310), pp. 241–244.
Bar-Ner et al. (1987) Blood (70), pp. 551–557.
Lider et al. (1989), J. Clin Invest. (83), pp. 352–356.
Klagsbrun et al. (1986) Proc. Natl. Acad. Sciences (83) pp. 2448–2452.
Bashkin et al. (1989), Biochemistry (28), pp. 1737–1743.
Vlodavsky et al (1987) Proc. Natl. Acad. Science, (84), pp. 2292–2296.
Rogelj et al (1988) Nature (321) pp. 173–175.
Vlodavsky et al (1983) Cancon Research (43), pp. 2709–2711.

Primary Examiner—Douglas W. Robinson
Assistant Examiner—Jeffrey J. Sevingny
Attorney, Agent, or Firm—Pennie & Edmonds

[57] ABSTRACT

The present invention relates to a substantially purified heparanase obtained from the human SK-HEP-1 cell line and a method to purify the heparanase from a centrifuged dialyzed homogenate of the SK-HEP-1 cells or a cell culture medium containing the heparanase from the SK-HEP-1 cell line.

39 Claims, 12 Drawing Sheets

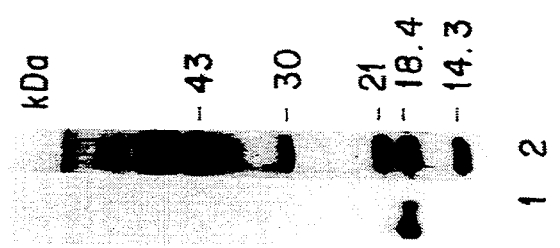
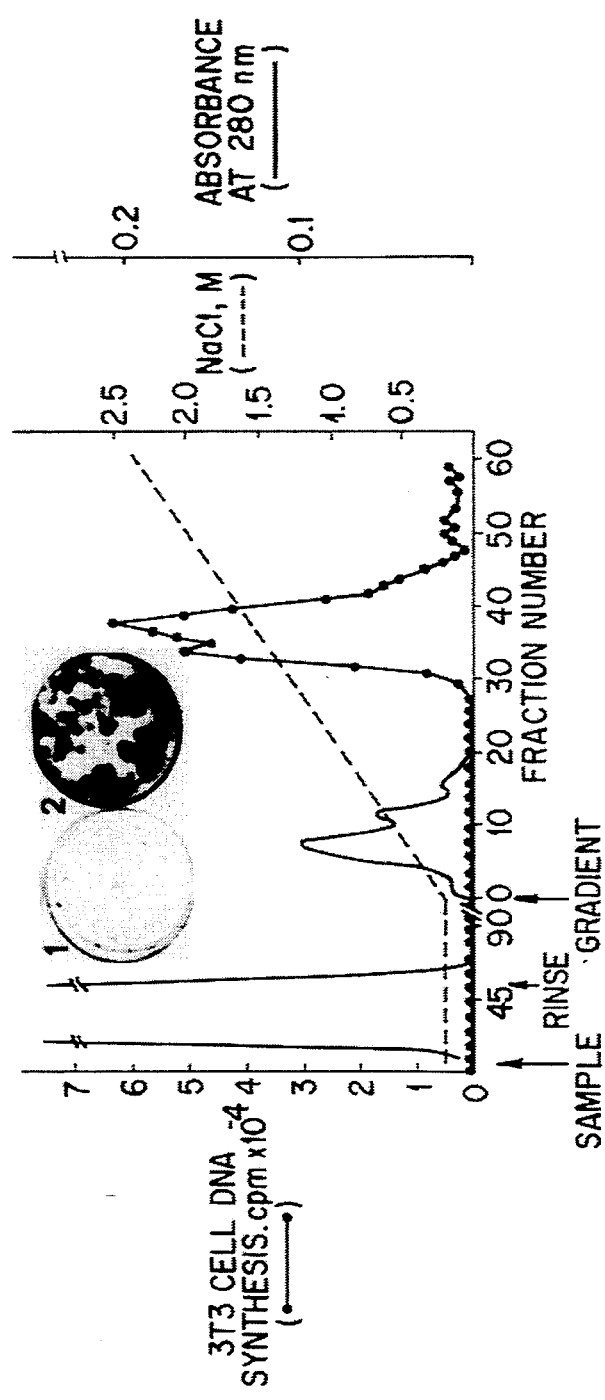

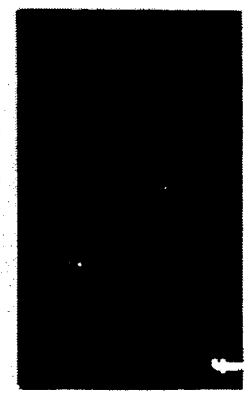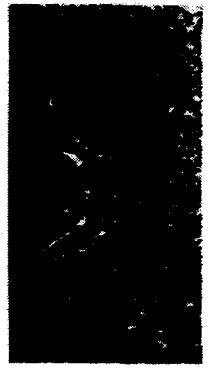
FIG. 2C(a) FIG. 2C(b) FIG. 2C(c) FIG. 2C(d) FIG. 2C(e) FIG. 2C(f)

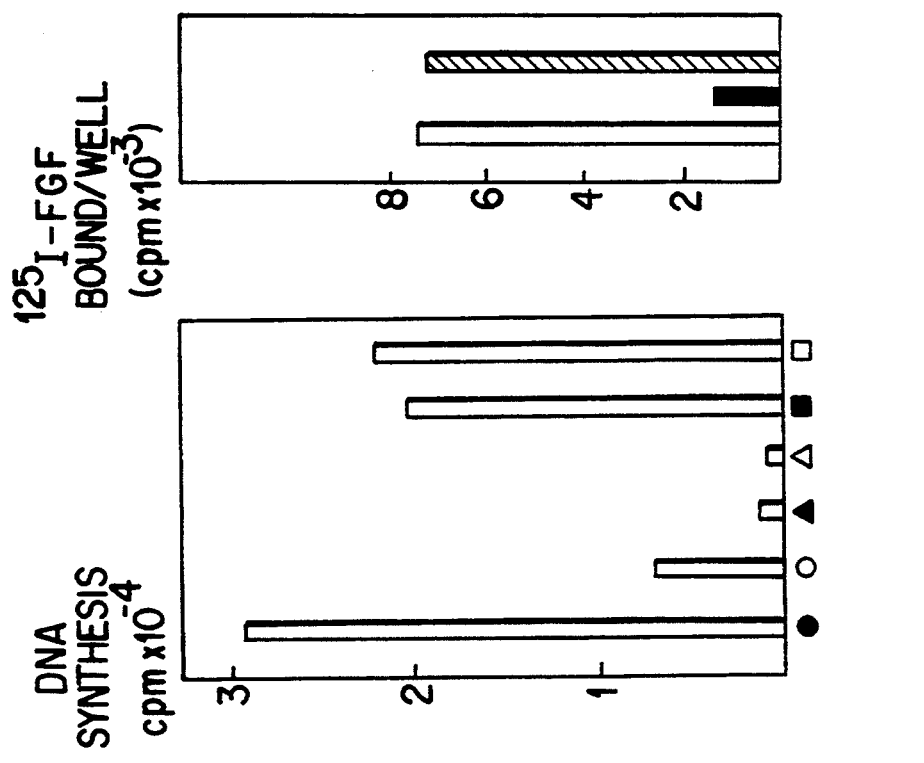
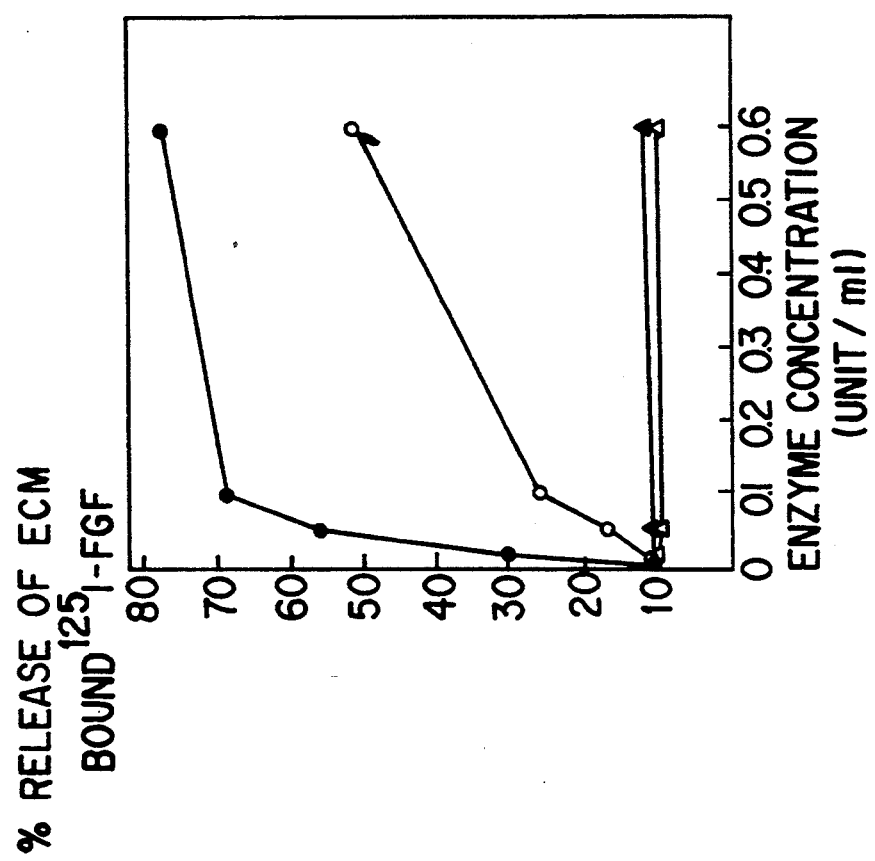
FIG. 3A(C)
FIG. 3A(B)
FIG. 3A(A)

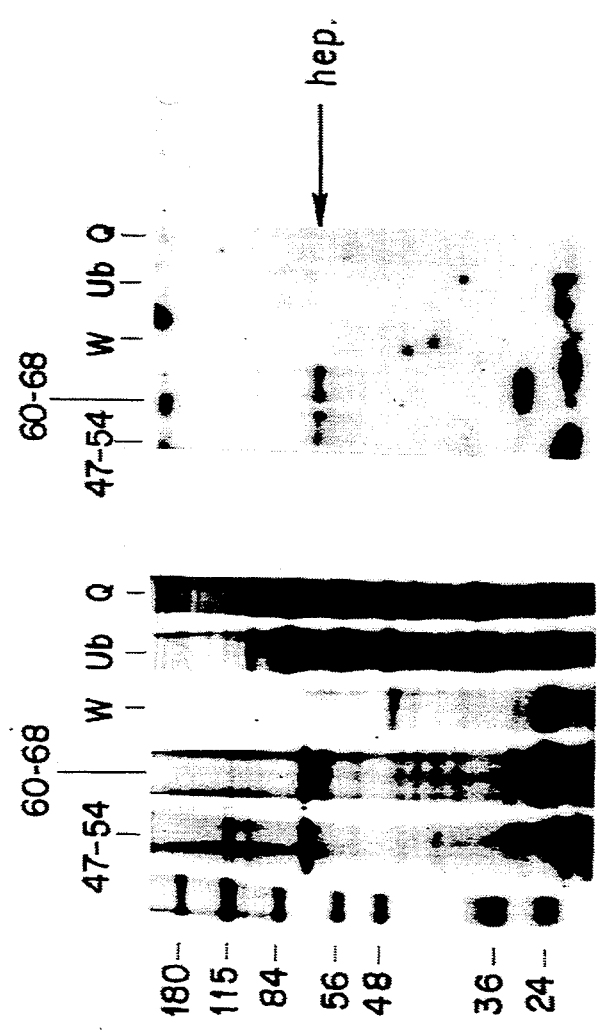

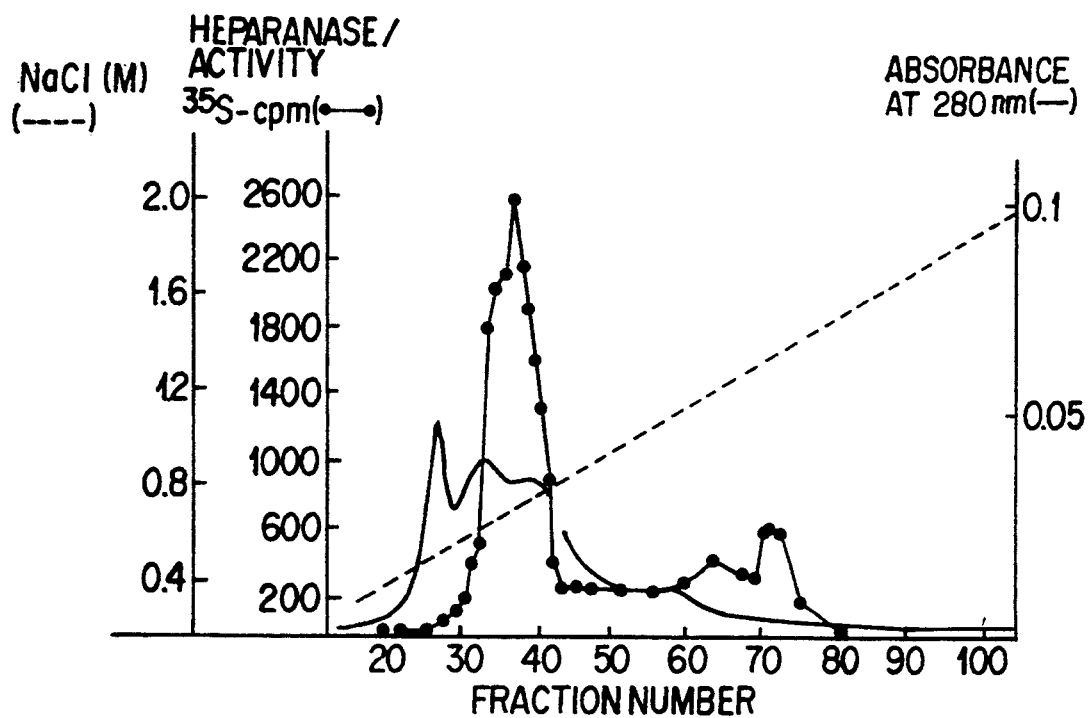
FIG. 5B
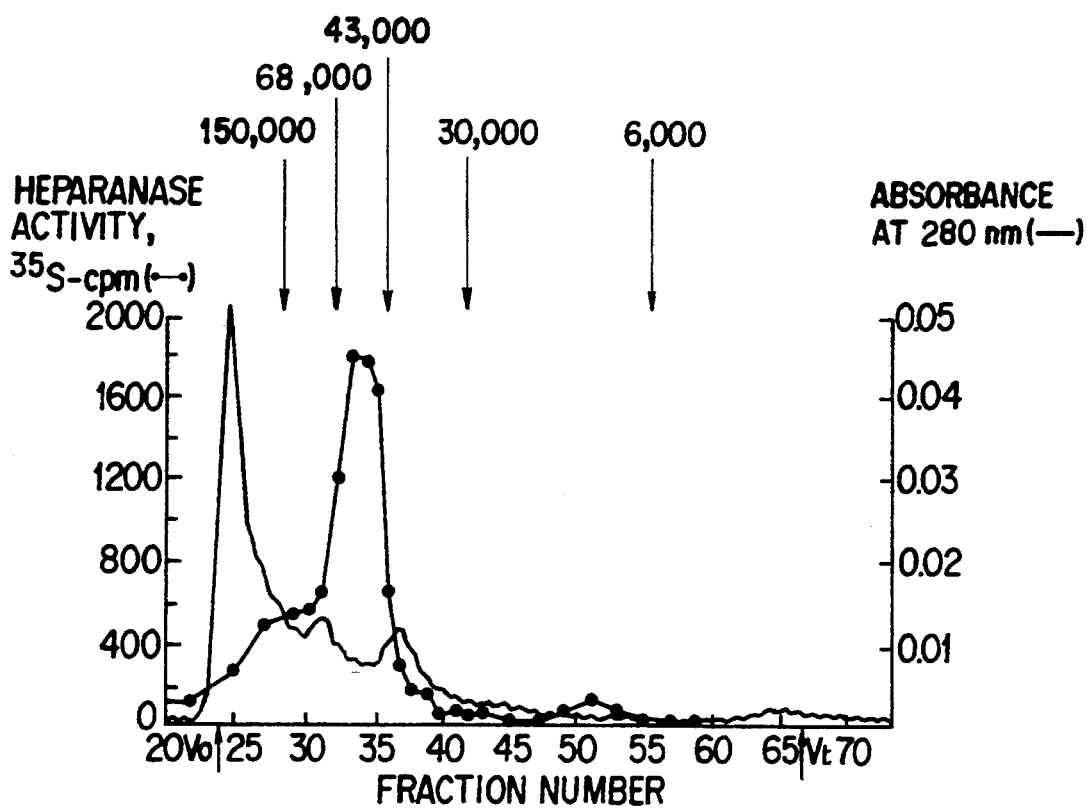
FIG. 5C, I

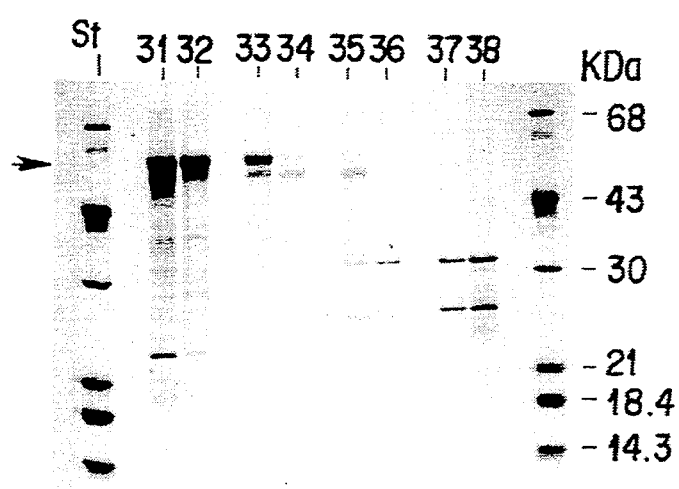
FIG. 5C,II

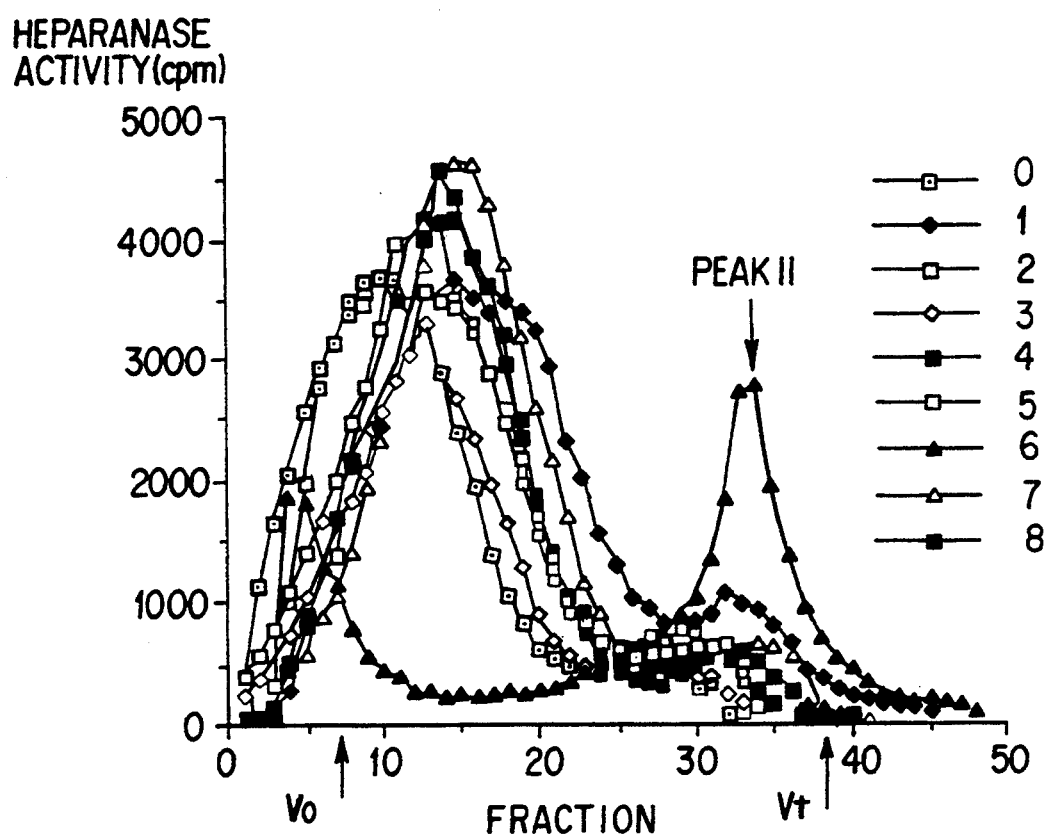
FIG. 6
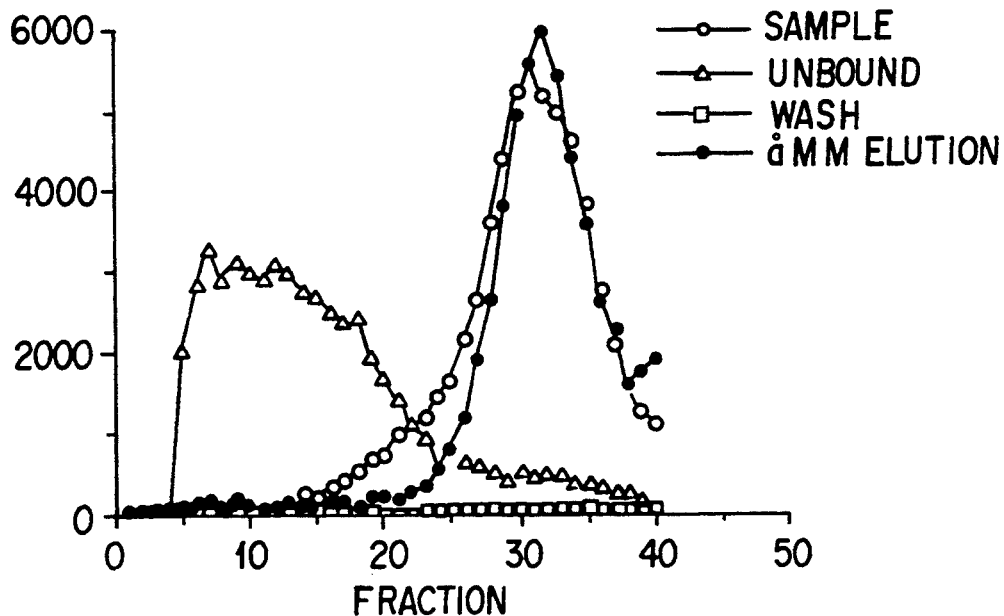
FIG. 5D, I

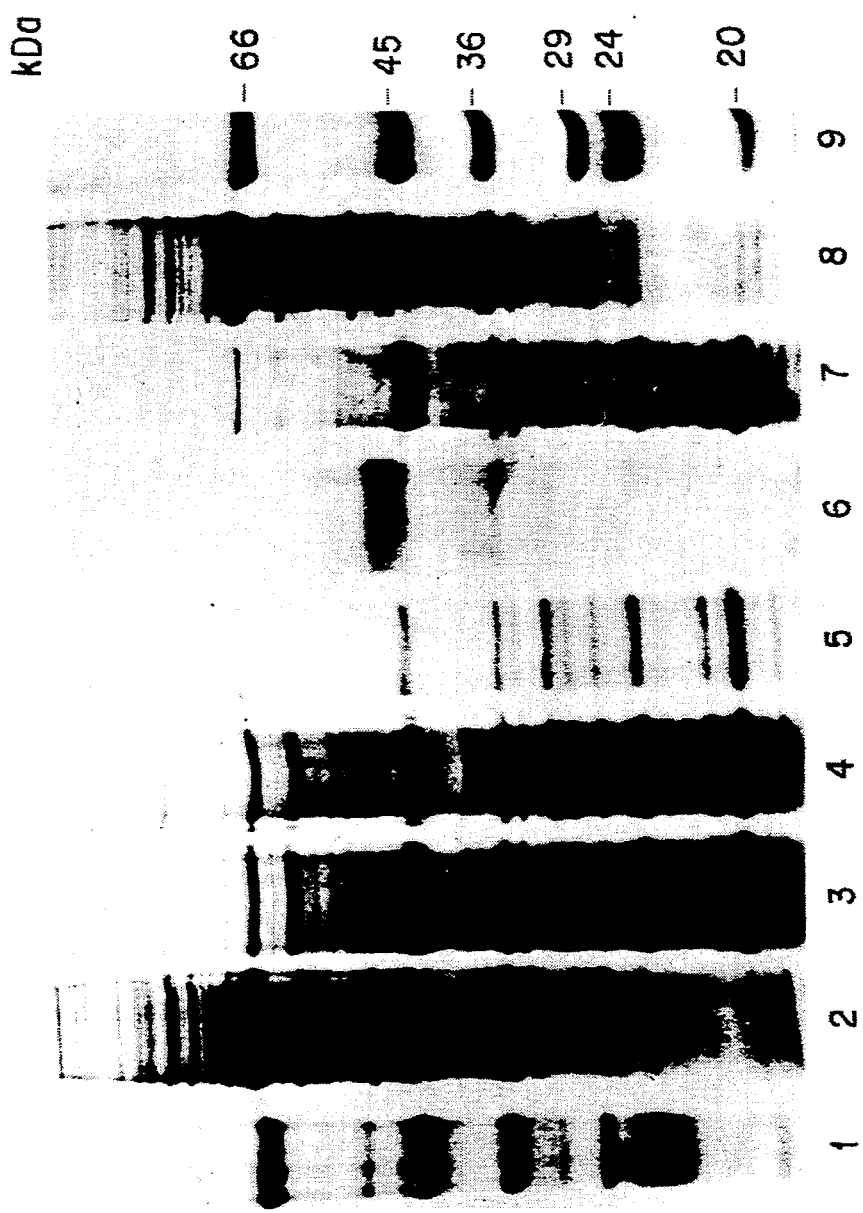
FIG. 5D, II

HEPARANASE DERIVED FROM HUMAN SK-HEP-1 CELL LINE

This application is a continuation-in-part of Ser. No. 07/397,554, filed Aug. 23, 1989, now abandoned.

1. FIELD OF THE INVENTION

The present invention relates to methods and compositions for stimulating the process of wound healing. More specifically, the invention relates to a method of promoting wound healing utilizing compositions comprising a purified form of heparanase.

2. BACKGROUND OF THE INVENTION

2.1. Heparan Sulfate and Related Compounds

The plasma membrane, extracellular matrix, and basement membranes of all tissue types contain, among other constituents, complex macromolecules referred to as heparan sulfate proteoglycans (HSPG). Their function in biological processes is believed to be varied: they appear to be involved in cell-cell recognition, tissue differentiation and morphogenesis, organization of extracellular matrix, permaselective properties, and cell-substrate adhesion. The extracellular matrix appears to be essential to the control of cell proliferation and morphogenesis, and HSPG, as a principal component of basement membranes, plays an integral role in tissue architecture and function.

Proteoglycans are high molecular weight compounds with a protein backbone; linked to the backbone are a number of side chains of different types of heteropolysaccharides. A high proportion of the molecular weight may thus be attributed to carbohydrates. These compounds can routinely be broken down by a number of different enzymes. The degradation of the proteoglycans usually begins with the proteolytic cleavage of the backbone to produce peptide components and glycosaminoglycans. The latter are in turn hydrolysable into smaller glycosaminoglycan fragments by endoglycosidase enzymes, and these are further degradable into monosaccharides by exoglycosidases. Heparan sulfate proteoglycans have an intimate interrelationship with the other macromolecules which make up the extracellular matrix, and thus, their degradation may have a profound effect on the regulation of cell anchorage, movement, function and growth.

2.2. HSPG Degradation

A number of normal and abnormal physiological conditions and disorders have now been shown to be associated with the degradation of the extracellular matrix of various tissues. For example, neutrophil mobilization, as part of the inflammatory process, requires that the cells penetrate the endothelium of blood vessels and the underlying basal lamina in order to reach the target tissue. The penetration requires the specific and mild action of readily released enzymes (i.e., heparanase) expressed by the neutrophils under conditions which maintain the integrity of the vessel wall (Matzner et al., *J. Clin. Invest.* 76:1306–1313, 1985). Similarly, in the process of metastasis, tumor cells must invade the basal lamina of the vascular endothelium in order to be transported to other sites in the body. T-lymphocytes as well, in responding to the presence of an antigen, will penetrate the walls of blood vessels and subendothelial extracellular matrix. Cell invasion is typically achieved by enzymatic breakdown of the matrix surrounding the cells. The invading cells must, therefore, be capable of producing ECM degrading enzymes whenever necessary to achieve penetration of the wall of the blood vessel or other target tissue.

Since a number of proteoglycans are known to exist as part of the connective tissue, the degrading enzyme could theoretically be any one of a number of enzymes which attack a particular sulfated proteoglycan. For example, depending on the specific tissue involved, the ECM may contain chondroitin sulfate, dermatan sulfate, hyaluronate, keratan sulfate or heparan sulfate, in a characteristic combination. Each of these can be broken down by, respectively, chondroitinase, hyaluronidase, keratanase or heparanase. The ability of a given cell to penetrate a particular tissue type, then, is dependent to a large extent in the production, by the cell, of an enzyme or enzymes which can degrade the proteoglycans in the tissue. HSPG interact with various macromolecules in the ECM, such as collagens, laminin and fibronectin. This suggests a key role for this proteoglycan in the structural integrity, self-assembly and insolubility of the ECM. Because of this property and because HSPG is the major proteoglycan of basement membranes, its degradation is necessary to allow penetration of cells through blood-vessels and epithelial basement membranes.

It has recently been observed that a certain type of endoglycosidase is produced by particular kinds of cells. For example, migrating human neutrophils have been shown to degrade heparan sulfate by secretion of heparanase, (Matzner, et al., supra). The same type of enzyme has been shown to be produced by metastatic melanoma cells (Nakajima et al., *J. Biol. Chem.* 259:2283–2290, 1984; Vlodavsky et al., *Exptl. Cell Res.* 140:149–159, 1982) and metastatic lymphoma cells (Vlodavsky et al., *Cancer Res.* 43:2704–2711, 1983). Antigen-stimulated T-lymphocytes also secrete heparanase, shortly after the exposure to antigen (Naparstek et al., *Nature* 310:241–243, 1984; Fridman et al., *J. Cell. Physiol.* 130:85–92, 1987). The endoglycosidase heparanase thus appears to play an integral role in a number of specific physiological functions, such as tumor metastasis (by way of aiding in invasion of blood vessels, basement membranes, and ECM) and autoimmune disorders (by aiding in extravasation of activated cells in the immune system). The use of heparanase inhibitors in impeding tumor metastases and autoimmune disorders has previously been suggested (WO 88/01280, 1988).

Biochemical analysis of HS degradation products revealed that the melanoma cell heparanase cleaves $\beta$-D-glucuronosyl-N-acetylglucosaminyl linkages in HS (Nakajima et al., *J. Biol. Chem.* 259:2283–2290, 1984). The melanoma and liver endo-$\beta$-D-glucuronidases appear to degrade HS but not heparin. In contrast, the human platelet enzyme depolymerizes both HS and heparin and an endoglucuronidase from a mouse mastocytoma exhibits strict specificity towards macromolecular heparin proteoglycan.

2.3. Angiogenic Factors

In addition to the functions noted above for heparanase, it has also been noted that this enzyme has the effect of causing release of angiogenic endothelial cell growth factors from basement membranes and subendothelial ECM (Vlodavsky et al., *PNAS USA* 8.4:2292–2296, 1987; Folkman et al., *Am. J. Pathol.* 130:393–400, 1988; Bashkin & Vlodavsky, *Biochemistry*, 2.8:1737-1743, 1989. "Angiogenesis" refers to the process of formation of new blood vessels, which accompanies a number of normal and abnormal physiological processes in the body. For example, angiogenesis typically accompanies the process of tumor formation, as well as the process of tissue repair in wound healing. Recently, a number of angiogenic factors have been discovered to occur naturally in many tissues of the body (Folkman and Klagsbrun, Science 235:442-447, 1987). Angiogenin, for example, is a polypeptide shown to have angiogenic activity in a rabbit cornea and chick embryo. Its mode of activity is uncertain, but it has been suggested that it causes release of endothelial mitogens or chemoattractants from host cells, or mobilizes macrophages to release these factors. Transforming growth factors (TGF) are also polypeptides which alter the behavior of fibroblasts and other cells in culture, and exhibit angiogenic activity in vivo (Folkman and Klagsbrun, supra). Other factors, such as low molecular weight endothelial mitogens, endothelial cell chemotactic factors, and certain lipids, such as prostaglandins, have been shown to be angiogenic but, as yet, their mode of activity is poorly characterized. None of these aforementioned factors have been shown to have any relationship to heparanase.

2.3.1. Fibroblast Growth Factor

Another group of factors, known as fibroblast growth factors (FGF) and endothelial cell growth factors (ECGF) are distinguished from these other angiogenic compounds by their ability to bind heparin with high affinity (Lobb et al. J. Biol. Chem. 261:1924-1928, 1986). Heparin is a well known compound which has been found to be circumstantially associated with angiogenesis in many different situations, but its direct role in the process is as yet unclear. However, these heparin-binding growth factors have been more directly implicated in the process. These factors were among the first to be so identified; FGF encompasses two classes of polypeptides, cationic or basic FGF, and anionic or acidic FGF, with ECGF being an extended form of acidic FGF. Both types of heparin-binding growth factors have been shown to stimulate endothelial cell migration and growth both in vitro and in vivo, and also appear to induce the formation of highly vascularized granulation tissue (Shing et al., J. Cell. Biochem. 29: 275-287, 1985).

An interesting aspect of these highly active factors is that they are virtually ubiquitous in normal living tissue, and yet endothelial proliferation in these tissues is quite low. This observation is consistent with the theory that the factors exist in a bound, inactive state in tissue and are only infrequently released. This belief has recently been verified, and it has now been shown that basic FGF is stored within the basement membrane (Folkman et al., Am. J. Pathol. 130:393-400, 1988). Evidence strongly supports the idea that FGF, within the ECM (FIGS. 1A and 1B) and basement membranes of the cornea (FIGS. 2A through 2C) and around blood vessels, is bound to heparan sulfate (Bashkin et al., Biochemistry, 28:1737-1743, 1989), thereby sequestering the growth factors from their site of action, until some exogenous factor causes its release (FIGS. 3A(A) through 3C).

2.3.2. Wound Healing

In addition to its role in angiogenesis and stimulation of endothelial cell migration and growth, FGF, as its name implies, also is essential in the proliferation of fibroblasts and virtually all other mesoderm and neuroectoderm-derived cells. Fibroblasts are mesenchymal connective tissue cells which are responsible for the production of collagen fibers, one of the major building blocks of connective tissue. Both the endothelial and fibroblast proliferation are essential elements of the process of wound healing. When an injury occurs, a number of events, involving many different cell types, occur shortly thereafter. White blood cells, particularly phagocytic white blood cells, are rapidly attracted to the site to clean the wound by removing foreign particles, including microbes. At the same time, fibroblasts appear in large numbers in the area, and begin laying down collagen, in the process of preparation and replenishment of connective tissue. The region is also invaded by endothelial cells, forming new capillaries to supply the new tissue with nutrients and to remove waste from the area. Eventually, the damaged tissue is completely replaced by new tissue and epithelial cells migrate from all sides to eventually cover the surface. Poorly healing wounds, or non-healing wounds (ulcers), occur in many clinical settings, including atherosclerosis and diabetes; as side effects of treatments associated with steroid therapy, immunotherapy, radiotherapy and chemotherapy; in pressure sores; and as a result of a variety of injuries in the elderly. Burns represent a special kind of non-healing wounds. While the commonest cause of poor healing is infection, other major factors include failure to recruit mesenchymal cells and failure to develop and maintain an adequate blood supply. For this reason, mitogens found to attract and promote proliferation of mesenchymal cells in vitro and to induce neovascularization in vivo, are under intensive study as wound healing agents (Lobb, Euro. J. Clin. Invest. 18:321-326, 1988).

Given an understanding of the mechanisms involved in wound healing, it appears that FGF may play a significant role in the process, by way of its effect on angiogenesis, as well as its effect on fibroblast growth. The ability to control its release, or to stimulate its production, could have profound effects on improving the wound healing process. However, at this time no known method has effectively utilized FGF in enhancing the healing process. Although recombinant FGF is known, it resembles various human oncogene products (Thomas, TIBS 13:327-328, 1988) and may, in some circumstances, initiate cell transformation (Rogelj et al., Nature 331:173-175, 1988). High doses of FGF have also been shown to be toxic to various cell types, including endothelial cells.

As noted above, the FGF is bound in situ in the extracellular matrix (ECM) to heparan sulfate, and can be released by the addition of heparanase to the ECM. Addition of heparanase may thus provide an effective method to mobilize and activate the ECM-bound FGF and hence to promote the wound healing process. The use of heparanase to release FGF from its natural setting has the advantage of the cells' responding locally to the endogenous natural growth factor and in appropriate amount. However, the preparations of heparanase that are currently known are too crude to be used therapeutically in displacing FGF from the connective tissue in which it is bound. A relatively pure heparanase is required before this enzyme can be contemplated for use in vivo in humans. Pathological conditions other than wound healing, which are likely to benefit from neovascularization promoted by FGF include cardiac, cerebral and peripheral ischaemic diseases and diseases associated with vascular damage, such as diabetes, hypertension and systemic lupus erythematosus. Other potential clinical applications for angiogenic factors are in processes such as ovulation, hair growth, transplantation, nerve regeneration and bone and cartilage repair.

3. SUMMARY OF THE INVENTION

The present invention provides a substantially purified heparanase, and a method of producing it. The purified heparanase is prepared by subjecting a cell extract containing heparanase, to cation exchange chromatography on CM-Sephadex, followed by affinity chromatography on heparin-Sepharose and/or ConA-Sepharose and gel filtration through Sephadex G-100.

The heparanase so produced has a purity of at least 4000-fold over the crude cell extract. This purified heparanase provides the basis for useful pharmaceutical compositions, comprising the purified heparanase in combination with a pharmaceutically acceptable, preferably slow releasing, carrier. Such a composition is useful for the treatment of wounds, and enhancement of the wound-healing process. It is also useful for the treatment of any other physiological state or condition in which neovascularization or angiogenesis would be expected to be of benefit. Wound treatment can be achieved by administration to an afflicted individual an effective amount of the composition of the present invention.

4. BRIEF DESCRIPTION OF THE FIGURES

FIGS. 1A and 1B illustrate: Heparin-Sepharose chromatography, mitogenic activity and electrophoretic transfer blot of ECM-derived bFGF: a) ECM extracts applied to heparin-Sepharose and growth factor activity eluted with salt gradient. Insert: bovine aortic EC seeded at clonal density and cultured in the absence (1) or presence (2) of ECM-derived growth factor; FIG. 1B: electrophoretic transfer blot: active fractions eluted from heparin-Sepharose subjected to SDS-PAGE, Western Blotting and staining with antiserum directed against an internal sequence (positions 33–43) of bFGF (lane 1).

Figure 2A:
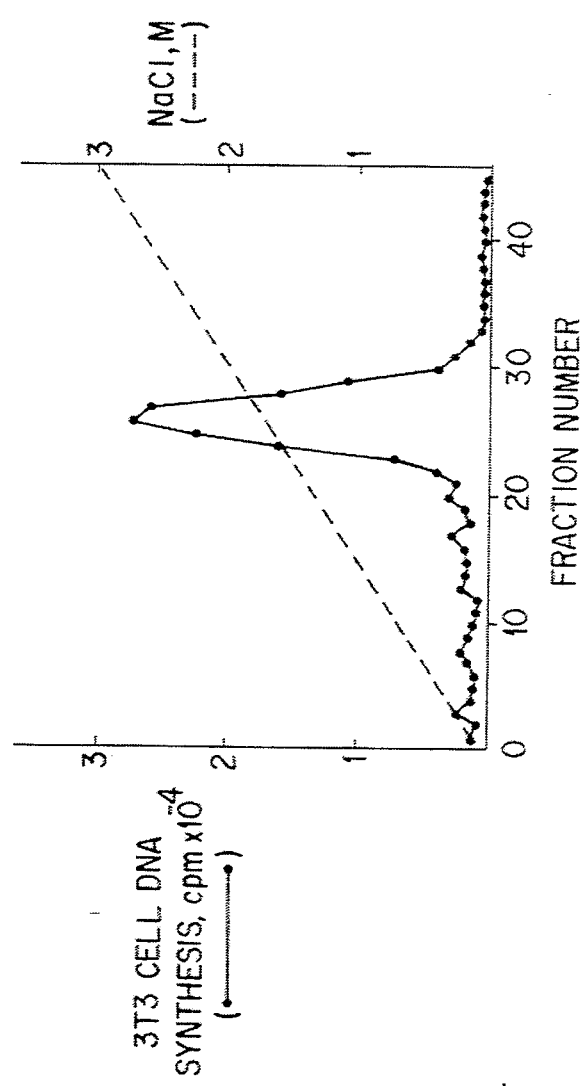

FIGS. 2A, 2B and 2C illustrate: Basic FGF-like growth factor is stored within basement membranes of the cornea: FIG. 2A: heparin-Sepharose chromatography of extracts from Descemet's membranes (30 corneas); FIG. 2B: electrophoretic transfer blot of active fractions eluted from heparin-Sepharose and derived from Descemet's membrane (lane 2) or from the outer portion (lane 1) of bovine corneas and subjected to SDS-PAGE, blotting and staining with antiserum against an internal sequence of bFGF; FIG. 2C, panels a through f immunofluorescence (Ab against internal sequence of FGF) FIG. 2C, panels b,d,f and corresponding phase contrast FIG. 2C, panels a,c,e micrographs of bFGF within frozen section of normal bovine corneas: FIG. 2C, panels a,b: outer aspect of Bowman's membrane; entire thickness of Descemet's membrane; FIG. 2C, panel f: staining of Descemet's membrane in the presence of a 10-fold excess of soluble antigen (synthetic peptide 33–43 of bFGF).

FIGS. 3A(A) through 3C illustrate: Heparanase-mediated release of ECM-bound FGF.

FIGS. 3A(A), 3A(B) and 3A(C): Release of ECM-bound FGF by various purified ECM degrading enzymes. FIG. 3A(A): ECM-coated wells were incubated (90 min, 22° C.) with $^{125}$I-bFGF, washed and treated with heparanase ( ), heparinase (o), chondroitinase ABC ( ), or chondroitinase AC ( ). Radioactivity released into the incubation medium is expressed as % of total ECM-bound $^{125}$I-FGF. "Spontaneous" release in the presence of buffer alone was 5%–7% of the total ECM-bound FGF; FIG. 3A(B) ECM-coated 4-well plates were incubated (90 min, 22° C.) with bFGF, washed and treated (0.1 units/ml, 60 min, 37° C.) with heparanase ( ), heparinase (o), chondroitinase ABC ( ), hyaluronidase (Δ), collagenase ( ) or trypsin ( ). Aliquots (20 ul) of the incubation medium were tested for stimulation of DNA synthesis in growth-arrested 3T3 cells; FIG. 3A(C) ECM-coated 4-well plates were untreated ( ) or pretreated with heparanase (0.1 u/ml, 60 min, 37° C.) ( ) or chondroitinase ABC (0.5 u/ml, 60 min, 37° C.) ( ). ECM was washed, incubated (90 min, 22° C.) with $^{125}$I-FGF, and the amount of ECM-bound FGF was determined.

Figure 3B:
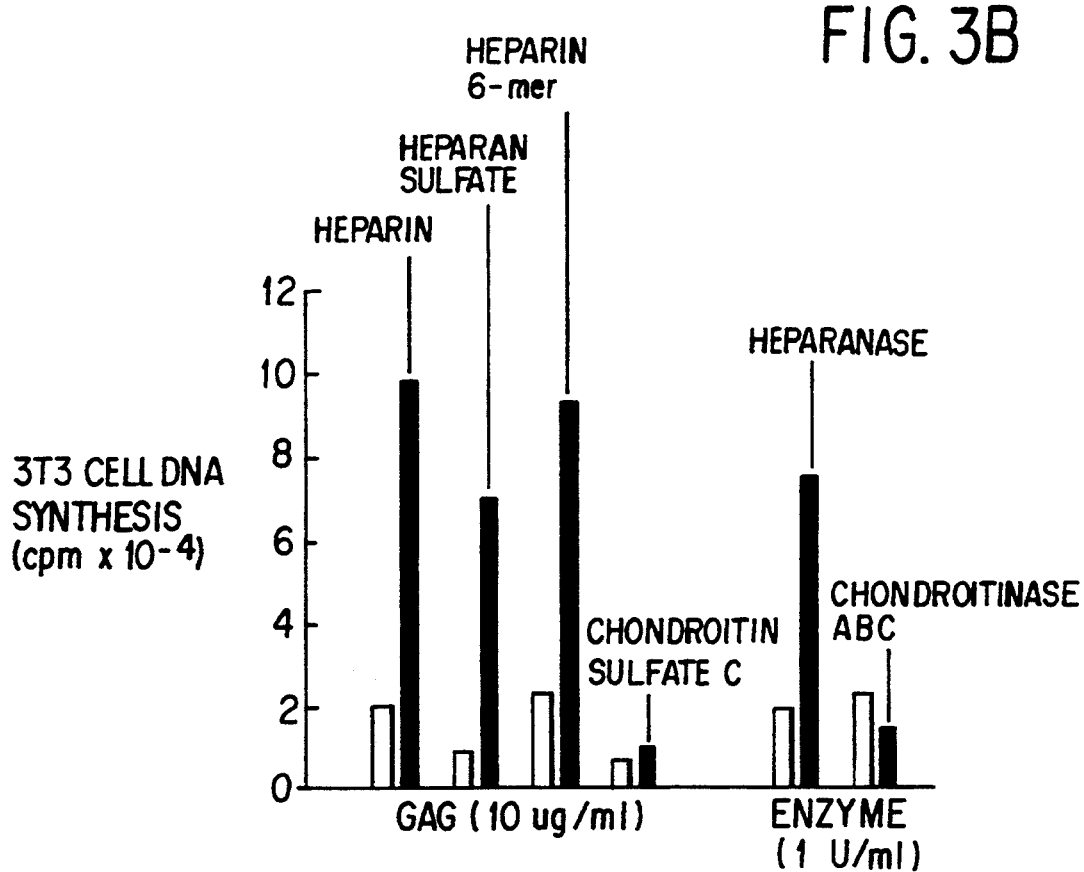

FIG. 3B: Release of endogenous bFGF from basement membranes of the cornea in vivo. White bars represent pooled halves of inner layers of corneas that were incubated for 1 hour at 24° C. in RPM1 medium alone. Each corresponding black bar represents the other halves of these corneas incubated in RPMI containing 10 μg/ml of a glycosaminoglycan (either heparin, heparan sulfate, a hexasaccharide fragment of heparin, or chondroitin sulfate C), or 1 U/ml of heparanase or chondroitinase/ABC. Mitogenic activity released by these treatments was inhibited by polyclonal anti-bFGF antibodies.

Figure 3C:
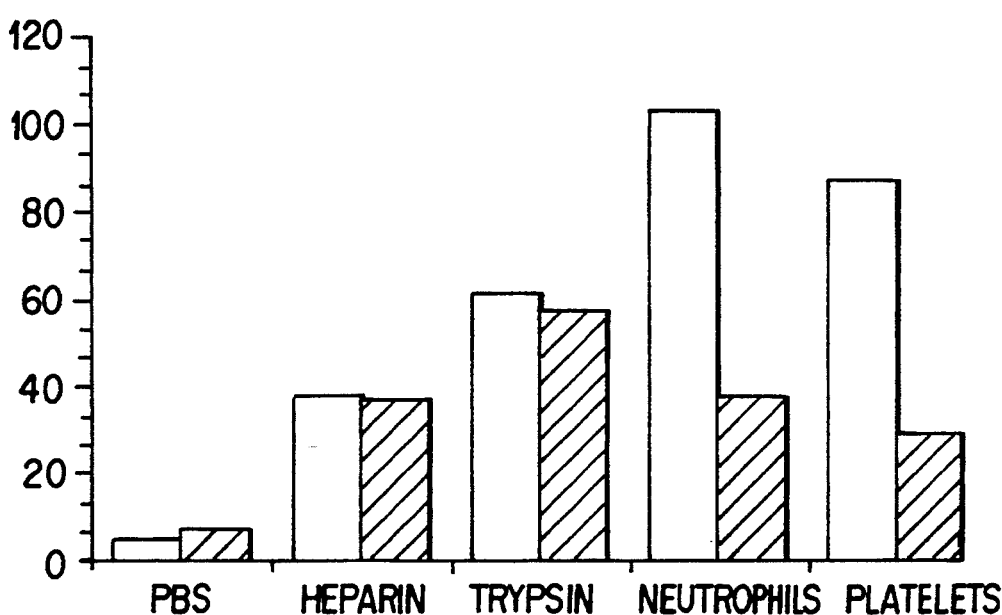

FIG. 3C: Release of ECM-bound FGF by the platelet and neutrophil heparanases. ECM-coated wells were incubated with $^{125}$I-FGF, washed and incubated with either heparin, trypsin, human neutrophils or platelets, in the absence ( ) and presence ( ) of carrageenan lambda (10 μg/ml), an inhibitor of heparanase. Release of FGF by platelets and neutrophils, but not by trypsin or heparin, was inhibited by carrageenan.

Figure 4:
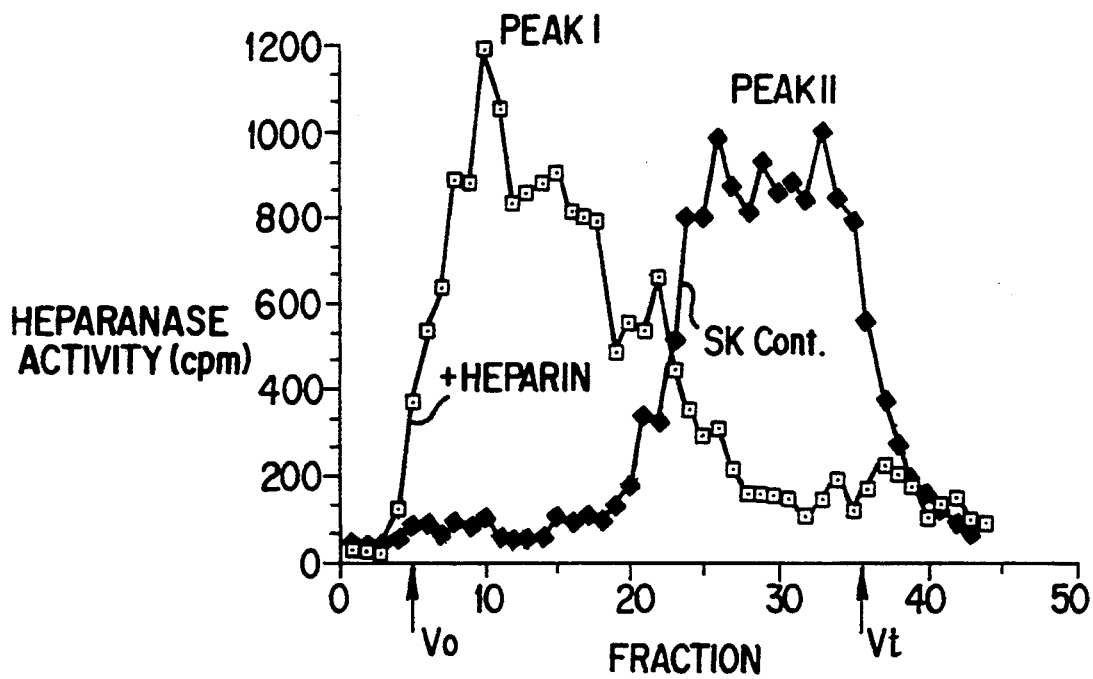

FIG. 4: Heparanase activity in lysates of Sk-Hep-1 cells. Sk-Hep-1 cells ($2 \times 10^6$) were lyzed by 3 cycles of freezing and thawing, centrifuged, and the supernatant fraction incubated (24 hours, 37° C., pH 6.2) with sulfate-labeled ECM in the absence ( ) and presence ( ) of 10 μg/ml heparin, an inhibitor of heparanase activity. Degradation products released into the incubation medium were analyzed by gel filtration on Sepharose 6B. Peak I: Nearly intact HS-proteoglycan; Peak II: HS degradation fragments released by heparanase.

Figure 5A:
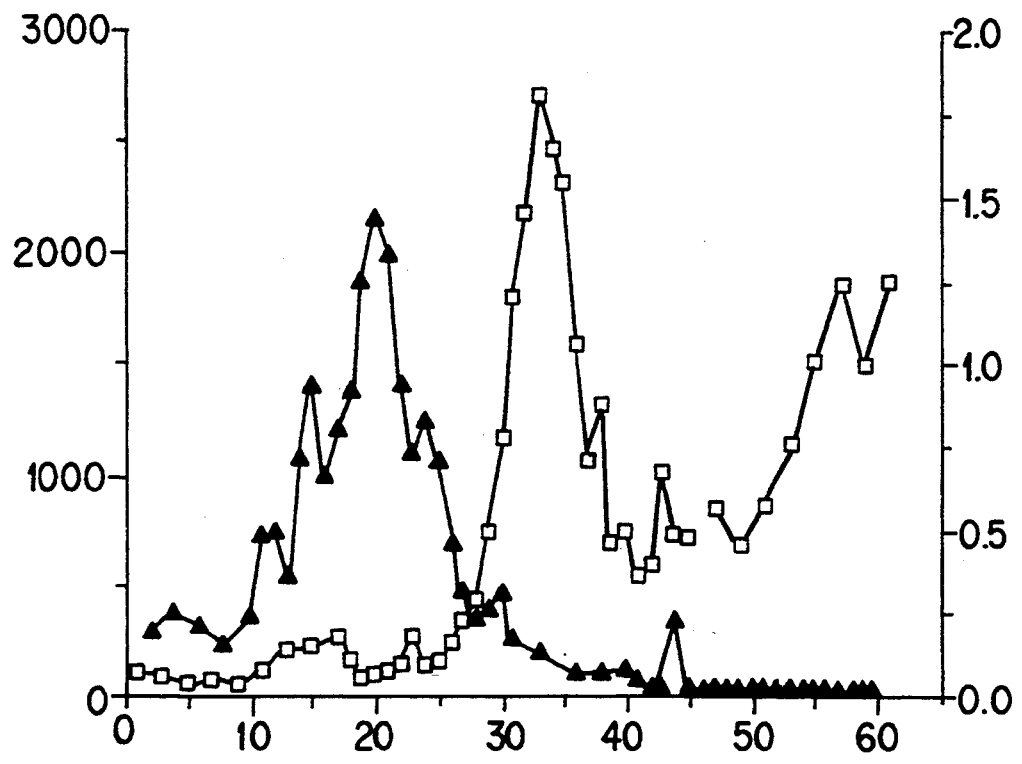

FIGS. 5AI through 5DII illustrate the various stages of purification of heparanase.

FIG. 5AI: CM-Sephadex chromatography. Material eluted from Biorex 70 at 0.5M NaCl was dialyzed against 20 mM NaCl, 10 mM citrate phosphate buffer, pH 5.8, and applied onto CM-50 column (6×20 cm). Heparanase activity was eluted with a linear gradient of 0.01M–1M NaCl, and each fraction measured for heparanase activity ( ) and protein concentration ( ).

FIG. 5AII: Polyacrylamide gel electrophoresis & "Western" blot analysis of column fractions. Starting material (Q), unbound material (Ub), wash through material (W) and pooled fractions (#47–54 and 60–68) eluted from CM-Sephadex with a salt gradient, were subjected to SDS/PAGE and "Western" immunoblot analysis. FIG. 5AII(A): Coomassie blue staining of the polyacrylamide gel; FIG. 5AII(B): Immobilon-P transfer membrane incubated with a 1:500 dilution of rabbit anti-heparanase antiserum and stained by successive incubations with biotinylated goat anti-rabbit antibodies, peroxidase-conjugated strepavidin, and 4-chloronaphtol substrate.

FIG. 5B: Heparin-Sepharose chromatography. Active material eluted from CM-Sephadex was adjusted to a salt concentration of 0.35M NaCl in 10 mM sodium acetate, pH 5.3, and applied to a heparin-Sepharose column (2×12 cm). Heparanase activity ( ) was eluted with a gradient of 0.4-1.2M NaCl.

FIG. 5CI: Sephadex G-100 chromatography.

Fractions eluted from heparin-Sepharose and containing heparanase activity (34-41) were pooled, dialyzed against 0.2M ammonium formate, and lyophilized. Lyophilized material was suspended in 2 ml 0.5M NaCl, 10 mM sodium acetate, pH 5.5, and applied to a Sephadex G-100 column (1×110 cm). Heparanase activity ( ) was eluted with the same buffer.

FIG. 5CII: SDS-PAGE and silver nitrate staining pattern of individual fractions (31-38) eluted from Sephadex G-100. Aliquots (200 μl) from each fraction were dialyzed, lyophilized and electrophoresed on SDS/7%-15% polyacrylamide gel.

FIG. 5DI: Con-A-Sepharose chromatography. Active fractions eluted from CM-Sephadex were dialyzed against buffer A (1M NaCl, 10 mM sodium acetate pH 6.0, 1 mM $MgCl_2$, 1 mM $CaCl_2$, and 1 mM $MnCl_2$) and applied to a Con-A-Sepharose column (2.5×6 cm). Starting material (o), unbound material (Δ), wash through material ( ), and material eluted with buffer A containing 0.2M alpha-methylmannoside ( ) were assayed for heparanase activity using sulfate labeled ECM as substrate.

FIG. 5DII: Polyacrylamide gel electrophoresis. Lane 1: MW markers; lanes 2 & 8: cell lysates; lanes 3 & 7: pooled active fractions eluted from CM-Sephadex; lane 4: Con A-Sepharose, unbound material; lane 5: wash through material; lane 6: Con A-Sepharose, material eluted with α-methylmannoside. The gel was stained with silver nitrate.

Figure 7A:
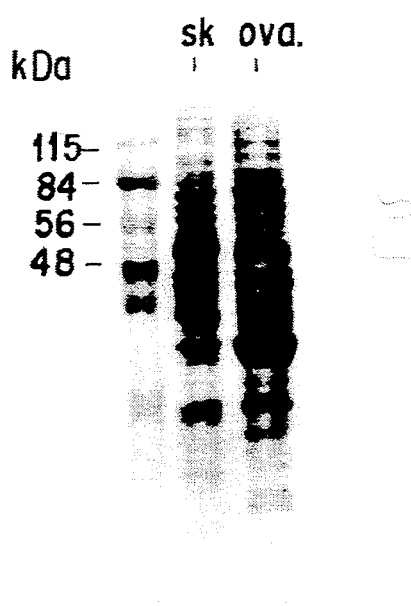
Figure 7B:
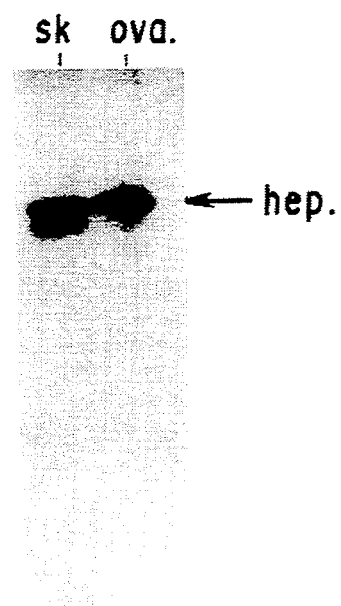

FIG. 6: Preparative native PAGE. Active fractions eluted from Con-A-Sepharose were pooled, dialyzed and applied to a native 8% polyacrylamide gel. The gel was cut into 5 mm strips (0-8) and heparanase activity in material electroeluted from each strip was assayed by gel filtration on Sepharose 6B of labeled degradation products released from sulfate labeled ECM. Material associated with strip #7 was injected into rabbits to produce the polyclonal anti-heparanase antibodies used in FIGS. 5AI through 5DII:

FIGS. 7A and 7B: Identification of heparanase in extracts of a biopsy specimen from a human ovarian tumor. Ovarian tumor removed at surgery was homogenized and the supernatant fraction subjected to FPLC gel filtration on superose 12 column. The starting material (lane 1) and fractions number 16-19 of the active peak (lanes 2-5) were subjected to SDS/PAGE and "Western" blot analysis. FIG. 7A: Coomassie blue staining of proteins electrotransferred to Immobilon-P transfer membrane. FIG. 7B: Autoradiogram of the same transfer membrane following successive incubations with rabbit anti-heparanase antibodies and $^{125}$I-goat anti-rabbit IgG.

5. DETAILED DESCRIPTION OF THE INVENTION

The present invention provides a substantially pure heparanase suitable for use in a pharmaceutical preparation. The heparanase produced by the present method represents at least a 4000-fold purification over the crude cell extracts.

5.1. Purification of Heparanase

Heparanase has been found to occur in many different cell types, e.g., metastatic melanoma cells (Vlodavsky et al., *Exptl. Cell Res.* 140:149-159, 1982; Nakajima et al., *Science* 220:611-612, 1983), neutrophils (Matzner, *J. Clin Invest.* 76: 1306-1313, 1985), T-lymphocytes (Naparstek et al., *Nature* 310:241-243, 1984; Fridman et al., *J. Cell Phys.* 130:85-92, 1987), or metastatic lymphoma cells (Vlodavsky et al., *Cancer Res.* 43:2704-2711, 1983). Extracts of any of these cell types can be used as a starting material for purification of heparanase. A cell line which produces significant amounts of heparanase in culture is the human hepatoma Sk-Hep-1 cells. (Klagsbrun et al., *PNAS USA* 83:2448-2452, 1986). The cell line Sk-Hep-1 is publicly available from the American Type Culture Collection as accession number HTB 52. The enzyme is secreted in relatively small amounts into the medium, so preparation of cell lysates is generally preferred. A crude heparanase extract may be obtained by homogenization of freezed and thawed cultured cells, centrifugation to pellet out the cell debris and subsequent collection of the supernatant.

A first step is contacting the heparanase containing supernatant with a cation exchange resin, preferably a weak cation exchange resin, such as carboxy-methyl Sephadex ™ or BioRex 70 ™. Bound heparanase is eluted from the column with a salt gradient. The eluted active fractions are then subjected to affinity chromatography. The fractions are applied to an appropriate group-specific adsorbent and the active fractions collected. Such an adsorbent is one which uses heparin as ligand, since heparanase has a strong affinity for heparin. An example of such a product is heparin-Sepharose CL-6B (Pharmacia). Particularly useful is a lectin affinity column, such as Con-A Sepharose (Pharmacia) provided that the sample is applied onto the column in the presence of 1M NaCl. After elution from the column of choice, the active fractions are pooled and the heparanase activity is recovered. The method by which the heparanase fraction is eluted depends upon the method of affinity purification. Elution from heparin-Sepharose is performed with a salt gradient and from Con-A Sepharose with 0.2M α-methyl mannoside. The Con-A Sepharose chromatography itself achieves a high yield and degree of purification. No further purification by this method is recommended for the proposed use in wound healing, due to a marked decrease in yield. With heparin-Sepharose chromatography, further purification may be required. Gel filtration on Sephadex G-100 of a heparin-sepharose purified sample further purifies the heparanase fraction to an acceptable level. A summary of these steps and the levels of purification at each step are shown in Table I. The products so produced are purified sufficiently to permit use in pharmaceutical formulations.

A platelet endo-β-D-glucuronidase has been partially purified by Oosta et al. (*J. Biol. Chem.* 257:11249, 1982). This enzyme is capable of degrading both HS and heparin and has a Mr of 134,000. Heparanase (Mr~96,000 dal) has also been partially reportedly purified from mouse B16-F10 melanoma cells by use of heparin-Sepharose, Con-A Sepharose and N-acetylated, N-desulfated heparin-Sepharose (Nakajima et al., *J. Cell.*

Biochem. 36:157–167, 1988, purification mentioned but not described).

TABLE Ia

Purification of Sk-Hep-1 Heparanase: Heparin-Sepharose Followed by Gel Filtration

|  | Total Protein (mg) | Total Activity* (units × 10$^6$) | Specific Activity (units/ug) | Fold Purification | Yield (%) |
|---|---|---|---|---|---|
| Cell lysates (dialyzed Sup.) | 1416 | 5.1 | 3.6 | 1 | 100 |
| Biorex (batch) | 216 | 4.5 | 20.8 | 5.8 | 88.2 |
| CM-Sephadex | 48.8 | 4.3 | 88.1 | 24.5 | 84.3 |
| Heparin-Sepharose | 1.4 | 0.52 | 71.4 | 103.2 | 10.1 |
| Sephadex G-100 | 0.0065 | 0.1 | 15385 | 4274 | 1.9 |

*1 unit = $\frac{\text{cpm (peak II)}}{1 - K_{av}}$

TABLE Ib

Purification of Sk-Hep-1 Heparanase: CM-Sephadex Followed by Con-A Sepharose

|  | Volume (ml) | Protein (mg/ml) | Total Protein (mg) | (%) |
|---|---|---|---|---|
| Cell lysates (crude extract) | 1050 | 2.366 | 2484 | 100 |
| Column load (dialyzed Sup.) | 1200 | 0.816 | 980 | 39.4 |
| Biorex (batch) | 350 | 0.617 | 216 | 8.7 |
| CM-Sephadex (active fractions) | 240 | 0.186 | 44.6 | 1.8 |
| Con-A-Sepharose (active fractions) | 4.2 | 0.112 | 0.47 | 0.019 |

Approximate recovery of activity - 75%
Approximate fold purification - 4000

5.2. Therapeutic Use

The purified heparanase, and the formulations containing same, may be used in therapy, in situations in which release of FGF from the extracellular matrix would be a desirable effect. More specifically, the heparanase formulations are useful in situations in which angiogenesis and/or the growth of fibroblasts is desired. A common situation in which the preparations would be useful for this purpose is for the stimulation and enhancement of wound healing.

In the present context, "wound" is intended to encompass any type of trauma which interrupts the integrity of the vascular system. This includes injuries to skin, such as cuts, burns, and ulcers. In view of the relatively large quantities of FGF-HS complexes known to exist in basement membranes of the cornea (Folkman et al., *J. Am. Pathol.* 130:393–400, 1988), local application of heparanase in the form of eye drops may be used particularly to accelerate repair of corneal ulcers. The application of purified heparanase to ischemic tissues is also expected to be beneficial, by increasing blood supply, and thus oxygen supply to these oxygen-deprived tissues. Heparanase can also be utilized in promoting bone healing by initiating neovascularization in a fractured area.

The therapeutically useful heparanase preparations may be combined with pharmaceutically acceptable carriers in the form of lotions, ointments, powders, or any other appropriate vehicle of application. The methods of preparing such formulations are well known to those skilled in the pharmaceutical art. Application of the active formulation can be continuous over a period of days or weeks, depending on the extent of the wound, and upon the speed of healing.

The utility of the purified heparanase is not limited to its therapeutic use. The availability of a purified enzyme provides a basis for preparation of specific anti-heparanase polyclonal and/or monoclonal antibodies. Availability of such antibodies will enable detection, quantitation and localization of heparanase in blood samples, body fluids, pleural effusions and biopsy specimens for diagnostic purposes. Such antibodies were, in fact, prepared in our laboratory against active heparanase eluted from a native polyacrylamide gel. These antibodies have been used for detection of heparanase in column fractions and biopsy specimens (FIGS. 5AII(A) and 5AII(B)).

6. EXAMPLES

6.1. Materials and Methods

The following sections describe the techniques employed in the experiments described in Section 6.2.

6.1.1. Cells

Cultures of bovine corneal endothelial cells were established from steer eyes as previously described (Vlodavsky et al., *Cancer Res.* 43:2704–2711, 1983). Stock cultures were maintained in DMEM (1 g glucose/liter) supplemented with 10% bovine calf serum, 5% FCS, penicillin (50 u/ml) and streptomycin (50 μg/ml) at 37° C. in 10% CO$_2$ humidified incubators. Partially purified brain-derived bFGF (100 ng/ml) was added every other day during the phase of active cell growth. Bovine aortic and capillary endothelial cells were cultured as described (Vlodavsky et al., *PNAS USA* 84:2292–2296, 1987).

6.1.2. Preparation of Dishes Coated with ECM

Bovine corneal endothelial cells were dissociated from stock cultures (second to fifth passage) with saline containing 0.05% trypsin and 0.02% EDTA, and plated into 4-well and 96-well plates at an initial density of 5×10$^4$ cells/ml. Cells were maintained as described above, except that FGF was not added and 5% dextran T-40 was included in the growth medium. Six to eight days after the cells reached confluency, the subendothelial ECM was exposed by dissolving (3 min, 22° C.) the cell layer with a solution containing 0.5% Triton X-100 and 20 mM NH$_4$OH in phosphate-buffered saline (PBS), followed by four washes in PBS. The ECM remained intact and firmly attached to the entire area of the tissue culture dish.

Culture dishes coated with sulfate-labelled ECM were prepared as described above, except that Na$_2$[$^{35}$S]O$_4$ (540 mCi/mmole) was added twice (40 uCi/ml) into the culture medium on the 3rd day after seeding, when the cells were nearly confluent, and 4 days afterward. The cultures were incubated with the labelled sulfate with no medium change and 10-12 days after seeding, the cell layer was dissolved and ECM prepared, as described (Vlodavsky et al., *Cancer Res.*, supra; Naparstek et al., *Nature* 310:241-243, 1984). 75%-85% of the ECM radioactivity was incorporated into HS.

6.1.3. Isolation of Heparan Sulfate from ECM

Heparan sulfate (HS) was isolated from unlabelled and sulfate-labelled ECM using methods described for isolation of HS from bovine aorta (Schmidt et al., *Eur. J. Biochem* 125:95-101, 1982) and swarm sarcoma basement membrane (Hassell et al., *PNAS USA* 77:4494-4498, 1980). For isolation of total glycosaminoglycans (GAGs), either labelled or unlabelled ECM is digested in 0.05M acetate buffer (pH 4.5) containing 0.5% papain, 0.05% EDTA and 0.005M cysteine at 65° C. for 24 hours, followed by alkaline degradation in 0.15% KOH for 4 hours at 37° C. and precipitation by cetylpyridinium chloride (CPC). The pellet containing mostly HS, dermatan sulfate and chondroitin sulfate is digested with 0.8 mU chondroitinase ABC in 10 ml 0.5M Tris buffer, pH 8.0, at 37° C. for 24 hours. A further 0.8 mU is added after the first 12 hours. The digest is precipitated with ethanol at a final concentration of 50% in the presence of 5% calcium acetate and 0.5M acetic acid. The precipitate is dissolved in and dialyzed against distilled water and reprecipitated several times with ethanol. Purification of HS is carried out by ion exchange chromatography on Dowex 1 X2 (200-400 mesh, chloride form) and elution with a continuous sodium chloride gradient (0.1-2.0M NaCl). HS is eluted at about 1.0M sodium chloride. HS containing fractions are pooled, exhaustively dialyzed against distilled water, and precipitated by two volumes of ethanol containing 1% potassium acetate (Schmidt et al., supra).

6.1.4. Assays for Heparanase Activity

6.1.4.1. Release and Characterization of HS Degradation Products

Cells, conditioned medium, or cell-free enzyme preparations are incubated (4-24 hours, 37° C., pH 6.0-6.5) with sulfate-labelled ECM. The reaction mixture is centrifuged (10,000 g, 5 min) and 0.5 ml aliquots of the supernatant are applied for gel filtration on Sepharose 6B columns (0.7×35 cm) equilibrated with PBS. Fractions (0.2 ml) are collected at a flow rate of 5 ml/h, and counted for radioactivity. The excluded volume (V$_o$) is marked by blue dextran, and the total included volume (V$_T$) by phenol red. Similar gel filtration profiles (K$_{av}$ values) are obtained by using ECM produced by corneal or vascular EC. Recoveries of labelled material applied to columns ranged from 85% to 95% in different experiments. Elution positions (Kav) of heparanase-mediated degradation products ranged from 0.5 to 0.75, depending on the source of enzyme and incubation conditions, but for a given enzyme preparation the variation in Kav values did not exceed +/− 15% in different determinations.

6.1.4.2. Use of Immobilized HS

Metabolically $^3$H-glucosamine- or Na$_2$$^{35}$SO$_4$-labelled HS is isolated from bovine aorta or ECM, as described above. Labelled HS is coupled to AH-Sepharose (Pharmacia) with carbodiimide at pH 5.0 while gently stirring the reaction mixture at 4° C. for 24 hours. To remove the excess of uncoupled ligand, the gel is washed alternately with 0.2M NaHCO$_3$ buffer (pH 8.3) and 0.1M acetate buffer (pH 4) 4-5 times, each buffer containing 0.5M sodium chloride. The gel is washed several times with distilled water and stored at 4° C. Labelled immobilized HS (100 µl, 5×10$^3$ cpm) is incubated (4-24 hours, 37° C. with gentle agitation) with the test materials (cells, cell extracts, conditioned medium, purified heparanase) in a final volume of 0.5 ml PBS (pH 6.2) in the absence and presence of heparin (20 µg/ml). The reaction mixture is then centrifuged and radioactivity in the pellet and supernatant determined separately. Radioactivity released in the presence of heparin represents non-specific release or cleavage by enzymes other than heparanase. We have also used the solid phase heparanase substrate developed by Nakajima et al. (*Anal. Biochem.* 157:162-171, 1986) and prepared by cross-linking of partially N-desulfated and N[$^{14}$C or $^3$H] acetylated HS onto agarose beads via one covalent linkage (id.). For this purpose, labelled HS is first aminated at the reducing terminal with 2M ammonium acetate in the presence of 0.4M sodium cyanoborohydride in 50% methanol at 50° C. for 6 days. The aminated HS is then purified by gel filtration and incubated with 1 ml Affi-Gel. The coupling reaction is continued at 4° C. for 48 hours, and the beads reacted with 0.1M glycine monoethyl ester to remove noncovalently attached HS from the beads (id.).

6.1.4.3. Use of ECM-Coated Microtiter Plates

We are currently using microtiter plates (96 wells) coated with sulfate-labelled ECM for screening of heparanase activity in large numbers of fractions eluted in the course of enzyme purification. Samples (50-200 µl) are added to each well, the plate is incubated (4-12 hours) at 37° C., and the amount of released radioactivity is indicative of heparanase activity in each fraction. We have used this screening assay while purifying the hepatoma heparanase, and verified that the released radioactivity constitutes mostly HS degradation products (0.5<Kav<0.75) when applied onto Sepharose 6B. It is important to emphasize that, whenever possible, and particularly in studies with intact cells, we are performing the time-consuming bioassay of ECM degradation involving gel filtration analysis of HS degradation products. Requirements for degradation of HS in a multimolecular structure such as ECM differ from heparanase-mediated degradation of soluble HS (Matzner et al., *J. Clin. Invest.* 76:1306-1313, 1985).

6.1.5. Purification of Heparanase

For large scale culture of the human hepatoma cell line Sk-Hep-1 (Klagsbrun et al., *PNAS USA* 83:2448-2452, 1986), cells from four T-75 flasks are transferred to a 1-liter spinner flask and grown (DMEM, 10% calf serum) until they reach a cell density of about 10$^6$ cells/ml. The cells are subsequently passaged and grown in the same manner in 3-liter spinner flasks to produce about 1-2×10$^{10}$ cells/20 liters. Cells are harvested from suspension cultures by centrifugation, washed twice with PBS, resuspended in 1M NaCl, 0.01M Tris-HCl, pH 7.5, and frozen at −20° C. The frozen pellet is thawed, resuspended in 1 liter 1M NaCl, 0.01M Tris-HCl, pH 7.5, and homogenized in a Waring Blender for 3 minutes. The homogenates are centrifuged at 20,000 g for 20 minutes, the pellets discarded, and the supernatants are dialyzed against 0.1M NaCl, 0.01 1M Tris-HCl, pH 7.0, in preparation for column chromatography.

6.1.5.1. Column Chromatography a) Cation exchange chromatography. Dialyzed supernatants are applied to a Biorex 70 column (5×40 cm) and heparanase is eluted by batch with 0.5M NaCl. Active fractions are collected, pooled, and dialyzed against 20 mM NaCl, 10 mM phosphate citrate buffer, pH 5.8. Dialyzed material is applied onto carboxymethyl Sephadex (CM 50) column (6×20 cm) equilibrated with 10 mM phosphate citrate, 20 mM NaCl, pH 5.8. The column is washed with two bed volumes of the same buffer, and heparanase activity is eluted with a linear salt gradient (0.01M-1M NaCl) of 1 liter at a flow rate of 40 ml/hour at 4° C.

b) Heparin-Sepharose. Active fractions eluted from CM-Sephadex are pooled, adjusted to a salt concentration of 0.35M NaCl in 10 mM acetate buffer, pH 5.3, and applied to a 2×12 cm heparin-Sepharose column (Pharmacia) equilibrated with the same buffer. Heparanase is eluted with a gradient (320 ml) of 0.4–1.2M NaCl at 40 ml/hour at 4° C.

c) Con A-Sepharose. Active fractions eluted from CM-Sephadex are pooled and dialyzed against a solution containing 1M NaCl, 10 mM sodium acetate, pH 6.0, 1 mM $CaCl_2$, 1 mM $MgCl_2$, and 1 mM $MnCl_2$ (buffer A). Dialyzed material is applied at 24° C. onto a 2×6 cm Con A-Sepharose column. The column is washed with 3 bed volumes of buffer A, and heparanase is eluted with 4 bed volumes of buffer A containing 0.2M alpha-methylmannoside.

d) Gel filtration. Active fractions eluted from heparin-Sepharose are dialyzed against 0.2M ammonium formate, lyophilized, and suspended in 2 ml 0.5M NaCl, 0.01M sodium acetate, pH 5.5. This material is applied onto a Sephadex G-100 column (1.2×100 cm) equilibrated with the same buffer and eluted at a flow rate of 3 ml/hour. For molecular weight determination, the column is first calibrated with proteins of known MW (alcohol dehydrogenase, 150 Kd; albumin, 66 Kd; ovalbumin, 43 Kd; carbonic anhydrase, 29 Kd; and aprotinin, 6.4 Kd). The void volume is marked by blue dextran. Crude and partially purified preparations of heparanase were also subjected to HPLC size exclusion chromatography on TSK 200 and Superose 12 columns under non-denaturing conditions. For this purpose, lyophilized preparations were reconstituted in 200 ul of 0.15M NaCl, 0.01M citrate phosphate buffer, pH 6.0, and centrifuged at 12,000 g to remove insoluble material. The clarified supernatants were applied to the column and eluted at a flow rate of 1 ml/min. The column was first calibrated with proteins of known molecular weights.

6.1.6. Preparative Native Page

Active fractions eluted from Con A-Sepharose were pooled and dialyzed against 10 mM Tris-phosphate buffer, pH 6.7, containing 10 mM NaCl. Dialyzed material was concentrated and loaded on a 6×8×0.15 cm 8% native polyacrylamide gel (without SDS) that was prerun for 1 hour at 20 mA. Electrophoresis was conducted at 15 mA for 3 hours at 4° C. The gel was cut into 0.5 cm strips which were then subjected to electrophoretic elution.

6.1.7. Preparative Isoelectric Focusing

Active fractions eluted from CM-Sephadex were pooled and dialyzed against 1% glycine. Dialyzed material was centrifuged at 18,000 g for 30 minutes, the supernatant subjected to preparative isoelectric focusing, and each fraction tested for heparanase activity.

6.1.8. Gel Electrophoresis

SDS polyacrylamide gel electrophoresis and silver staining were performed as described in Vlodavsky et al. (*PNAS USA* 84:2292–2296, 1987).

6.2. Experimental Results

6.2.1. Heparanase Activity in Sk-Hep-1 Cells

Incubation (24 hours, 37° C., pH 6.2) of Sk-Hep-1 cells on sulfate-labelled ECM resulted in release of high Mr (approx. $0.5 \times 10^6$ Da) and low Mr ($5 \times 10^3 – 1 \times 10^4$ Da) labelled material which eluted from Sepharose 6B with Kav<0.2 (peak I) and 0.35<Kav<0.8 (peak II), respectively. A similar incubation of Sk-Hep-1 cell lysates with the labelled ECM resulted in release of mostly low Mr degradation products (Kav=0.72 on Sepharose 6B) (FIG. 4). These low Mr (approx. 8,000 dal) fragments were (i) 5–7 fold smaller than intact, ECM-derived HS side chains; (ii) resistant to digestion with papain or chondroitinase ABC; and (iii) sensitive to cleavage with nitrous acid—all characteristic features of an endoglycosidase (heparanase) produced HS degration fragments. About 90% of the released radioactivity was precipitated with 0.05% cetylpyridinium chloride in 0.6M NaCl, conditions that specifically precipitate heparan sulfate sequences. Furthermore, release of low Mr HS cleavage products was inhibited by heparin (FIG. 4), a potent inhibitor of heparanase-mediated HS degradation. These results indicate that heparanase is expressed by intact Sk-Hep-1 cells and that a much greater activity can be extracted from lysates of these cells. Medium conditioned by cultured Sk-Hep-1 cells contained only small amounts of heparanase activity. Hepatoma cell lysates were therefore used in subsequent experiments as a source for purification of the enzyme.

6.2.2. Cation Exchange Chromatography

Sk-Hep-1 cells cultured in spinner flasks to a density of $10^6$ cells/ml were harvested by centrifugation (250 g×10 minutes) and washed twice in phosphate buffered saline, pH 7.4 (PBS). The pellet of $1–2 \times 10^{10}$ cells was resuspended in 300 ml of 1M NaCl, 0.01M Tris-HCl, pH 7.5, and subjected to 3 cycles of freezing and thawing, followed by homogenization in a Waring Blender. The homogenates were centrifuged (20,000 g for 30 min), the supernatant dialyzed against 0.1M NaCl, 0.01M Tris-HCl, pH 7.0, and applied onto a Biorex 70 column (5×40 cm) for batch elution of the enzyme with 0.5M NaCl in 10 mM Tris pH 7.0. Active material was dialyzed against 10 mM phosphate citrate buffer, 20 mM NaCl, pH 6.0, centrifuged at 20,000 g for 30 minutes, and the supernatant applied onto a 6×20 cm CM-50 Sephadex column. Heparanase activity was eluted with a linear salt gradient (0.01M-1M NaCl in phosphate citrate buffer) at a concentration of 0.7–0.8M NaCl (5AII(A) and 5AII(B)). 50%–60% of the total protein applied onto the CM-Sephadex column did not bind to the column, and about 30% of the bound protein was eluted at a salt concentration lower than that which eluted the enzyme (Table Ia). For determination of heparanase activity in this and subsequent purification steps, samples (50 μl) of column fractions were first incubated (0.5–3 hours, 37° C., pH 6.0) with sulfate-labelled ECM in 96-well plates for measurements of released radioactivity. Heparanase activity in active fractions was then verified by gel filtration analysis of the released material on Sepharose 6B columns, as described.

Two approaches were applied for further purification of heparanase eluted from CM-Sephadex. In the first procedure, the enzyme was subjected to heparin-Sepharose affinity chromatography, followed by gel filtration on Sephadex G-100. The other procedure utilized Con A-Sepharose chromatography.

A 50 kDa type 1 plasminogen activator inhibitor (PAI-1) may be present as a contaminant with the heparanase. The presence of PAI-1 may be detected with PAI-1 antibodies that cross-react with the purified heparanase preparation in Western blot analysis. The following modification of the purification protocol separates the heparanase enzyme from PAI-1 protein. Active heparanase eluted from CM-Sephadex is rechromatographed on CM-Sephadex at pH 7.4 in the presence of 0.1% CHAPS. Most of the PAI-1 is eluted closely before the protein having heparanase activity.

6.2.3. Heparin-Sepharose and Gel Filtration

Active fractions eluted from CM-Sephadex were pooled, dialyzed against 0.35M NaCl, 10 mM sodium acetate, pH 5.3, and applied onto a 2×6 cm heparin-Sepharose column equilibrated with the same buffer. Unbound protein showing no heparanase activity was removed, and the column subjected to a linear gradient of 0.4–1.2M NaCl. Heparanase activity was eluted at a concentration of 0.7–0.8M NaCl as determined by release of labelled material from ECM-coated wells of a 96-well plate (FIG. 5B), and actual analysis of heparan sulfate degradation products on Sepharose 6B columns.

Gel filtration analysis (Superose 12, TSK-200) of heparanase preparations eluted from CM-Sephadex indicated a MW for heparanase in the range of 50–60 kD. Sephadex G-100 SF was therefore chosen as an appropriate resin for further purification and determination of the enzyme MW. For this purpose, fractions eluted from heparin-Sepharose were dialyzed, lyophilized and suspended in 1–2 ml of 0.5M NaCl in 0.01M sodium acetate, pH 5.5. As demonstrated in FIG. 5CI, heparanase activity was eluted as a single peak in fractions corresponding to a MW of about 50 kD (fractions 33–35). Estimated fold purification and yield of enzyme are presented in Table Ia. Samples of fractions 31–38 were subjected to SDS PAGE and silver staining to further assess the enzyme MW and degree of purification. A band corresponding to the expected MW (approx. 50 kD) correlated with heparanase activity in each of the fractions. Fraction #34, which exhibited the highest specific activity, contained, in addition to the major putative heparanase band, a protein of a slightly higher MW, and few proteins of lower MW which could barely be detected (FIG. 5CII).

If removal of PAI-1 is desired, the above procedure may be modified by conducting the heparin Sepharose chromatography at pH 7.4 in the presence of 1% CHAPS.

6.2.4. Con A-Sepharose Activity Affinity Chromatography

Preliminary studies indicated that the hepatoma heparanase binds to Con A-Sepharose and elutes with 0.2M alpha-methylmannopyranoside. A higher degree of binding specificity, resulting in a better purification of the enzyme, was obtained when 1M NaCl was included in the sample and elution solutions. For this purpose, active fractions eluted from CM-Sephadex were dialyzed against 1M NaCl containing 10 mM sodium acetate, pH 6.0, 1 mM $MgCl_2$, 1 mM $CaCl_2$, and 1 mM $MnCl_2$. More than 95% of the total sample protein did not bind to the column under these conditions, and heparanase could not be detected in either the unbound or column wash material. In contrast, 80%–90% of the total enzyme activity was recovered in the alpha-methylmannoside eluate containing <2% of the total protein which was loaded on the column (FIG. 5DI, Table Ib). SDS PAGE revealed the presence of a major doublet protein in the 50 kD region, in addition to some lower MW proteins, including the 27 kD subunit of the Con A molecule itself (FIG. 5DII).

In order to obtain a single band preparation, enzyme eluted from Con A-Sepharose was subjected to native polyacrylamide gel electrophoresis, as described in Materials and Methods. The gel was cut into strips of 5 mm, and protein was electroeluted from 5 mm segments of each strip. Heparanase activity, measured by gel filtration analysis of sulfate-labelled degradation products, was eluted primarily from strip #7. A much lower activity was detected in strip #4 (FIG. 6). Enzyme associated with strip #7 was homogenized with the polyacrylamide in a minimal volume of PBS, mixed with complete Freund's adjuvant, and injected into rabbits to produce polyclonal anti-heparanase antibodies. This material will also be subjected to amino acid sequencing for the purpose of gene cloning and expression. The anti-heparanase antibodies have been used to immunodetect the enzyme in "Western" blots of fractions eluted from CD-Sephadex (FIG. 5AII(B)) and Con-A Sepharose and in active fractions derived from a biopsy specimen of a human ovarian tumor (FIGS. 7A and 7B).

Further removal of PAI-1 may be accomplished by means of Mono-S (Pharmacia) high pressure liquid chromatography performed at pH 7.4 in the presence of 0.1% CHAPS. Heparanase is eluted by salt gradient (0.1M NaCl to 0.7M NaCl). When PAI-1 is separated from heparanase, the heparanase has a purity of at least 6,000-fold over a crude cell extract of heparanase, and preferably a purity of at least 8,000-fold over a crude cell extract of heparanase.

What is claimed is:

1. A heparanase formulation, obtained from the Sk-Hep-1 cell line wherein the heparanase has hydrolytic activity for heparan sulfate but not heparin and the specific heparanase activity of the formulation is at least 1000-fold greater than the specific heparanase activity of a centrifuged dialyzed cell homogenate prepared from the Sk-Hep-1 cell line.

2. The heparanase formulation of claim 1 wherein the specific heparanase activity of the formulation is at least 2000-fold greater than the specific heparanase activity of the homogenate.

3. The heparanase formulation of claim 1 wherein the specific heparanase activity of the formulation is at least 4000-fold greater than the specific heparanase activity of homogenate.

4. A heparanase formulation obtained from the human SK-HEP-1 cell line wherein the heparanase has hydrolytic activity for heparan sulfate but not heparin, the specific heparanase activity of the formulation is at least 1000-fold greater than the specific heparanase activity of a centrifuged dialyzed cell homogenate prepared from the SK-HEP-1 cell line, and the heparanase is obtained by the method comprising:
  (a) contacting a heparanase-containing centrifuged dialyzed homogenate Of cell line Sk-Hep-1 with a cation exchange resin, and obtaining a first active eluate;
  (b) contacting the first eluate with an affinity purification absorbent; and
  (c) recovering a second active eluate which contains heparanase to provide for said heparanase formulation.

5. The heparanase formulation of claim 4 wherein the affinity absorbent contains heparin.

6. The heparanase formulation of claim 4 wherein the affinity absorbent is a lectin affinity absorbent.

7. The heparanase formulation of claim 4 wherein the cation exchange resin is a weak cation exchange resin.

8. The heparanase formulation of claim 7 wherein the first eluate is obtained by elution of the exchange resin with a salt gradient.

9. The heparanase formulation of claim 8 wherein the gradient is a linear gradient of about 0.01—about 1M NaCl.

10. The heparanase formulation of claim 5 wherein the second eluate is eluted with a gradient of about 0.4–1.2M NaCl.

11. The heparanase formulation of claim 5 wherein the method further comprises subjecting the second eluate to gel filtration and recovering the heparanase formulation from the filtrate.

12. The heparanase formulation of claim 6 wherein the first eluate is applied to the lectin affinity adsorbent in the presence of at least 1M NaCl.

13. The heparanase formulation of claim 12 wherein the second eluate is obtained by elution with about 0.2M alphamethylmannoside.

14. The heparanase formulation of claim 4 wherein the specific heparanase activity of the formulation is at least 2000-fold greater than the specific heparanase activity of the homogenate.

15. The heparanase formulation of claim 4 wherein the specific heparanase activity of the formulation is at least about 4000-fold greater than the specific heparanase activity of the homogenate.

16. A method for preparing a heparanase formulation, which comprises:
  (a) obtaining a heparanase containing cell supernatant from the human Sk-HEP-1 line;
  (b) contacting the heparanase containing supernatant with a cation exchange resin, and obtaining a first active eluate;
  (c) contacting the first eluate with an affinity purification absorbent; and
  (d) recovering a second active eluate which contains heparanase to provide for said heparanase formulation.

17. The method of claim 16 wherein the cation exchange resin is a weak cation exchange resin.

18. The method of claim 16 wherein the affinity adsorbent contains heparin.

19. The method of claim 16 wherein the affinity absorbent is a lectin affinity adsorbent.

20. The method of claim 17 wherein the first eluate is obtained by elution of the exchange resin with a salt gradient.

21. The method of claim 20 wherein the gradient is a linear gradient of about 0.01 to about 1M NaCl.

22. The method of claim 18 wherein the second eluate is eluted with a gradient of about 0.4–1.2M NaCl.

23. The method of claim 18 which further comprises subjecting the second eluate to gel filtration and recovering the heparanase formulation from the filtrate.

24. The method of claim 19 wherein the first eluate is applied to the affinity absorbent in the presence if at least 1M NaCl.

25. The method of claim 24 wherein the second eluate is obtained by elution with about 0.2M alpha-methyl mannoside.

26. The method of claim 16 which is performed so that the specific heparanase activity of the second eluate is at least 2000-fold greater than a centrifuged dialyzed homogenate of the cell.

27. The method of claim 16 which is performed so that the specific heparanase activity of the second eluate is at least 4000-fold greater than a centrifuged dialyzed homogenate of the cell.

28. A heparanase formulation obtained from the human SK-HEP-1 cell line wherein the heparanase has hydrolytic activity for heparan sulfate but not heparin, the specific heparanase activity of the formulation is at least 1000-fold greater than the specific heparanase activity of a centrifuged dialyzed cell homogenate prepared from the SK-HEP-1 cell line, and the heparanase is obtained by the method comprising:
  (a) obtaining a heparanase-containing human SK-HEP-1 cell line culture medium;
  (b) contacting the heparanase containing medium with a cation exchange resin, and obtaining a first active eluate;
  (c) contacting the first eluate with an affinity purification absorbent; and
  (d) recovering a second active eluate which contains heparanase to provide for said heparanase formulation, wherein the heparanase is present in Sk-Hep-1.

29. The heparanase formulation of claim 28 wherein the affinity absorbent contains heparin.

30. The heparanase formulation of claim 28 wherein the affinity absorbent is a lectin affinity absorbent.

31. The heparanase formulation of claim 28 wherein the cation exchange resin is a weak cation exchange resin.

32. The heparanase formulation of claim 31 wherein the first eluate is obtained by elution of the exchange resin with a salt gradient.

33. The heparanase formulation of claim 32 wherein the gradient is a linear gradient of about 0.01—about 1M NaCl.

34. The heparanase formulation of claim 29 wherein the second eluate is eluted with a gradient of about 0.4–1.2M NaCl.

35. The heparanase formulation of claim 29, obtainable by the method which further comprises subjecting the second eluate to gel filtration and recovering the heparanase formulation from the filtrate.

36. The heparanase formulation of claim 30 wherein the first eluate is applied to the affinity adsorbent in the presence of at least 1M NaCl.

37. The heparanase formulation of claim 35 wherein the second eluate is obtained by elution with about 0.2M alphamethylmannoside.

38. The method of claim 16 wherein the cell supernatant is a centrifuged dialyzed cell homogenate.

39. The method of claim 16 wherein the cell supernatant is a cell line culture medium.

* * * * *